(12) United States Patent
Strobl et al.

(10) Patent No.: US 9,931,157 B2
(45) Date of Patent: Apr. 3, 2018

(54) METHODS AND DEVICES FOR CREATING THERMAL ZONES WITHIN AN ELECTROSURGICAL INSTRUMENT

(71) Applicant: Ethicon LLC, Guaynabo, PR (US)

(72) Inventors: Geoffrey S. Strobl, Williamsburg, OH (US); Alex Kiturkes, Union City, NJ (US); David C. Yates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 686 days.

(21) Appl. No.: 14/486,670

(22) Filed: Sep. 15, 2014

(65) Prior Publication Data

US 2016/0074095 A1   Mar. 17, 2016

(51) Int. Cl.
  *A61B 18/14* (2006.01)
  *A61B 18/00* (2006.01)
  *A61B 17/00* (2006.01)

(52) U.S. Cl.
  CPC ..... *A61B 18/1445* (2013.01); *A61B 2017/00831* (2013.01); *A61B 2018/0063* (2013.01); *A61B 2018/00071* (2013.01); *A61B 2018/00095* (2013.01); *A61B 2018/00101* (2013.01); *A61B 2018/00136* (2013.01); *A61B 2018/00196* (2013.01); *A61B 2018/00607* (2013.01); *A61B 2018/147* (2013.01); *A61B 2018/1455* (2013.01)

(58) Field of Classification Search
  CPC ... A61B 2018/00089; A61B 2018/00095; A61B 2018/00101
  See application file for complete search history.

(56) References Cited

U.S. PATENT DOCUMENTS

| 6,500,176 | B1 | 12/2002 | Truckai et al. |
| 6,533,784 | B2 | 3/2003 | Truckai et al. |
| 6,656,177 | B2 | 12/2003 | Truckai et al. |
| 6,770,072 | B1 | 8/2004 | Truckai et al. |
| 6,802,843 | B2 | 10/2004 | Truckai et al. |
| 6,905,497 | B2 | 6/2005 | Truckai et al. |

(Continued)

OTHER PUBLICATIONS

Written Opinion of the International Searching Authority for Application No. PCT/US2015/049988 dated Nov. 27, 2015.

*Primary Examiner* — Jaymi Della
(74) *Attorney, Agent, or Firm* — Mintz Levin Cohn Ferris Glovsky and Popeo, P.C.

(57) ABSTRACT

Surgical instruments and methods for controlling temperature are described herein and can have particular utility when sealing tissue. In one embodiment, an end effector can include first and second jaw members configured to clamp tissue therebetween, and an electrode having a single continuous conductive surface that is coupled to the first jaw member. The end effector can also include a plurality of electrical insulators of varying thermal conductivity disposed between the electrode and the first jaw member coupled thereto. The electrode can be divided into a plurality of thermal zones by at least one opening formed therein and the plurality of electrical insulators can be arranged such that at least a first thermal zone contacts an electrical insulator having a first thermal conductivity and at least a second thermal zone contacts an electrical insulator having a second thermal conductivity that is higher than the first thermal conductivity.

11 Claims, 12 Drawing Sheets

(56) References Cited

U.S. PATENT DOCUMENTS

| | | |
|---|---|---|
| 6,913,579 B2 | 7/2005 | Truckai et al. |
| 6,926,716 B2 | 8/2005 | Baker et al. |
| 6,929,644 B2 | 8/2005 | Truckai et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,169,147 B2 | 1/2007 | Nosel |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,311,709 B2 | 12/2007 | Truckai et al. |
| 7,354,400 B2 | 4/2008 | Asafusa et al. |
| 7,381,209 B2 | 6/2008 | Truckai et al. |
| 7,955,331 B2 * | 6/2011 | Truckai .............. A61B 18/1442 606/50 |
| 2003/0078578 A1 * | 4/2003 | Truckai .............. A61B 18/1442 606/51 |
| 2003/0199870 A1 * | 10/2003 | Truckai .............. A61B 18/1442 606/51 |
| 2005/0004570 A1 * | 1/2005 | Chapman ........... A61B 18/1442 606/51 |
| 2005/0159745 A1 * | 7/2005 | Truckai .............. A61B 18/1442 606/51 |
| 2008/0045942 A1 * | 2/2008 | Truckai .............. A61B 18/1442 606/40 |
| 2009/0076506 A1 | 3/2009 | Baker |
| 2009/0248022 A1 * | 10/2009 | Falkenstein ........ A61B 18/1442 606/51 |
| 2010/0036370 A1 | 2/2010 | Mirel et al. |
| 2011/0288369 A1 * | 11/2011 | Ginnebaugh ........ A61B 18/085 600/36 |
| 2012/0136347 A1 * | 5/2012 | Brustad .............. A61B 18/1445 606/33 |
| 2015/0223868 A1 * | 8/2015 | Brandt .............. A61B 18/1445 606/40 |

\* cited by examiner

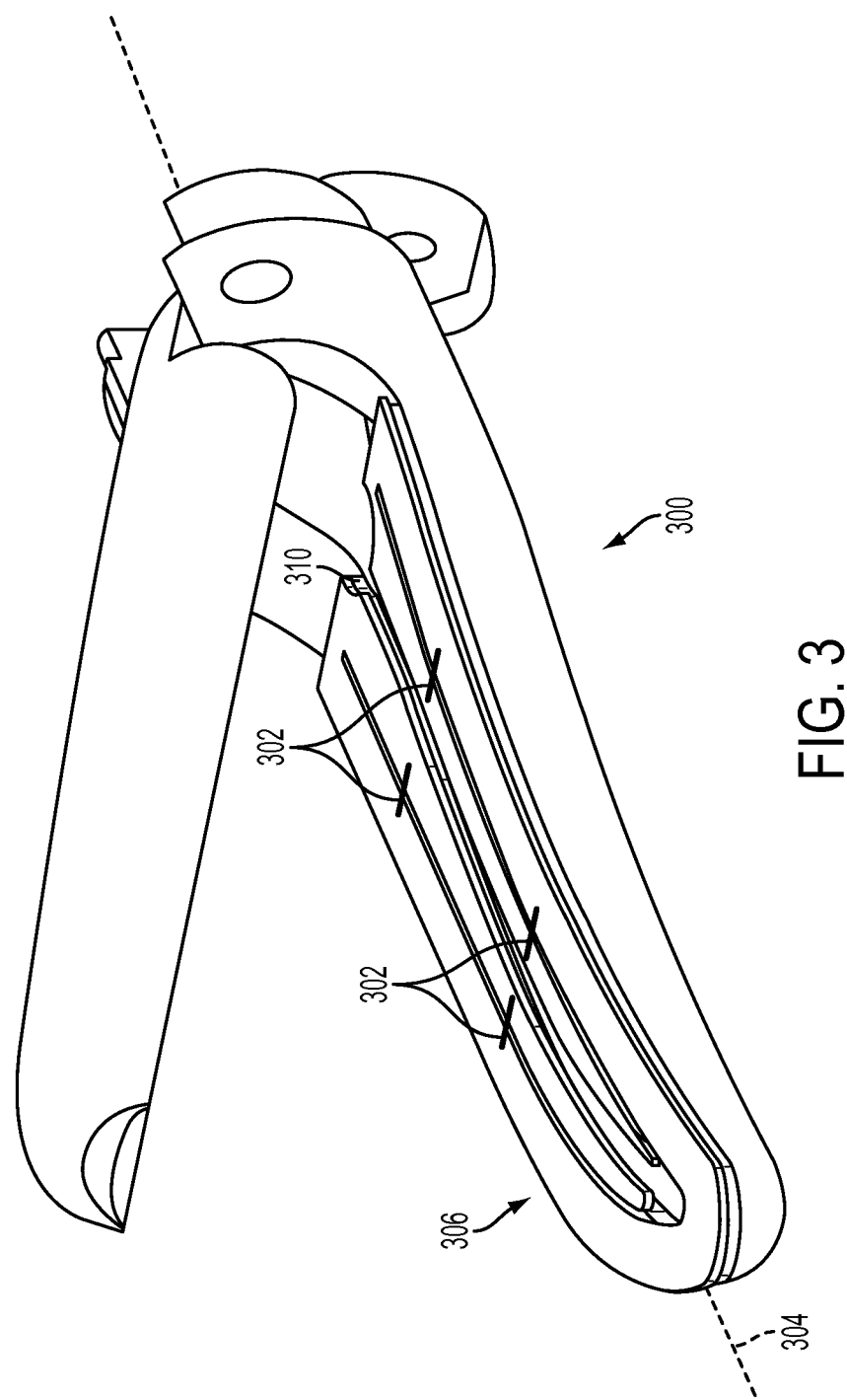

METHODS AND DEVICES FOR CREATING THERMAL ZONES WITHIN AN ELECTROSURGICAL INSTRUMENT

FIELD

The present invention relates to surgical devices and, more particularly, to electrosurgical devices for cutting and sealing tissue.

BACKGROUND

Various energy sources such as radiofrequency (RF) sources, ultrasound sources, and lasers have been developed to coagulate, seal or join together tissue volumes in open and laparoscopic surgeries. One method of tissue sealing relies upon the application of electrical energy to captured tissue to cause thermal effects therein for sealing purposes. Various mono-polar and bi-polar radiofrequency (RF) instruments and jaw structures have been developed for such purposes. In general, the delivery of RF energy to a captured tissue volume elevates the tissue temperature and thereby at least partially denatures proteins in the tissue. In a typical arrangement of a bi-polar radiofrequency (RF) jaw structure, each face of opposing first and second jaw members can include an electrode. RF current can flow across the captured tissue between electrodes in the opposing jaw members, denaturing many of the proteins in the captured tissue. Such proteins, including collagen, can be denatured into a proteinaceous amalgam that intermixes and fuses together as the proteins recombine. As the treated region heals over time, this biological "weld" can be reabsorbed by the body's wound healing process. Another method of tissue sealing relies upon the application of ultrasound energy to tissue captured between jaw members. The application of ultrasound energy to the captured tissue can likewise elevate the temperature of the captured tissue and thereby similarly denature proteins in the tissue.

Performance of tissue sealing surgical instruments can vary based on several factors and the design of such an instrument can be driven by competing desires. For example, the instrument must be capable of sealing the targeted tissue as described above, but surgeons or other users also want to minimize the time necessary to form the seal, as well as the amount of collateral tissue damage due to lateral thermal spread through tissue outside of the jaw members. Applying a high level of energy rapidly can form a seal quickly, but can also result in excess heating of the instrument electrodes via resistive heating or conduction of heat from the tissue into the electrodes. Excessively hot electrodes can begin sticking to tissue and cannot be repositioned without damaging tissue unless they are first allowed to cool for a period of time. Reducing the amount of energy applied to the tissue to address this problem, however, can increase the time to form a seal and can result in greater thermal spread through tissue over that time.

In addition, the particular configuration of the surgical instrument plays a role the management of thermal energy. For example, if an instrument's electrodes are thermally insulated from the jaws and other structure, the time to cool excessively heated electrodes before repositioning can increase significantly. Conversely, if there is good thermal conduction between an electrode and the remainder of the instrument, heat can be more efficiently transferred away from the treatment site, but this can increase the time to form a seal and result in increased thermal spread through adjacent tissue.

Accordingly, there is a need for improved devices and methods for managing thermal energy during tissue sealing operations.

SUMMARY

The present invention addresses these and other needs by providing surgical instruments that optimize thermal energy management through the creation of thermal zones over the area of an electrode or other active element. More particularly, the devices and methods described herein can divide an electrode into a plurality of thermal zones of varying temperature (or varying thermal conductivity). Dividing an electrode in this manner can allow for the concentration of high temperatures where they are most desired, while simultaneously allowing thermal energy to be conducted or wicked away from areas where it is not as desired. As a result, the thermal energy created during the sealing operation can be optimally managed and a high quality tissue seal or weld can be created.

In one aspect, a surgical end effector can include first and second jaw members movable relative to one another between an open position and a closed position to clamp tissue therebetween, as well as an electrode having a single continuous conductive surface that is coupled to the first jaw member such that the electrode contacts tissue clamped between the first and second jaw members when in the closed position. The end effector can further include a plurality of electrical insulators of varying thermal conductivity that are disposed between the electrode and the first jaw member coupled thereto. Further, the electrode can be divided into a plurality of thermal zones by at least one opening formed therein and the plurality of electrical insulators can be arranged such that at least a first thermal zone contacts an electrical insulator having a first thermal conductivity and at least a second thermal zone contacts an electrical insulator having a second thermal conductivity that is higher than the first thermal conductivity.

The devices and methods described herein can have a number of additional features and/or variations, all of which are within the scope of the present invention. For example, in various embodiments the plurality of thermal zones can have any of a variety of shapes and sizes, and can be arranged relative to one another in a number of different ways. For example, in some embodiments the at least first thermal zone and the at least second thermal zone can extend along a longitudinal axis of the end effector, and the at least second thermal zone can be positioned laterally of the at least first thermal zone. This can create an effect of varying the thermal conductivity, and therefore the temperature during operation, in a medial-lateral direction relative to a longitudinal axis of the end effector. Such an arrangement can provide, for example, a thermal zone of lower temperature (i.e., higher thermal conductivity), along an outer edge of an end effector, while a thermal zone of higher temperature (i.e., lower thermal conductivity) can be created along a central or inner portion of the end effector. Lowering the temperature in a thermal zone near an outer edge of the end effector can decrease the amount of lateral thermal spread that can damage tissue outside of the jaw members.

In other embodiments, decreasing lateral thermal spread can be accomplished by reversing the above configuration such that at least first thermal zone can be positioned laterally of the at least second thermal zone. This can create a thermal zone of higher temperature (i.e., lower thermal conductivity) along the outer edge of the end effector, while a thermal zone of lower temperature (i.e., higher thermal conductivity) can be created along a central or inner portion of the end effector. In such an embodiment, thermal spread to tissue outside the jaws can be reduced due to the fact that the impedance of the tissue increases as it is heated, and rapidly increasing the impedance of tissue on the outer edge of the electrode can create a barrier that contains current delivered to tissue contacting the inner portion of the electrode.

Still other arrangements are possible as well. For example, in some embodiments the at least first thermal zone and the at least second thermal zone can be positioned alternately along a longitudinal axis of the end effector. In such an embodiment, the at least first and second thermal zones can extend for the full width of the electrode, and can thereby create a repeating series of hotter and cooler zones extending along the length of the end effector.

In still other embodiments, it can be desirable to create either a high temperature (i.e., low thermal conductivity) zone or a low temperature (i.e., high thermal conductivity) zone at a distal end of the end effector. For example, creating a high temperature zone in this location can provide surgeons an easy way to perform touch-ups after a sealing operation. Conversely, in some embodiments creating a low temperature zone in this location can allow a surgeon to grasp and manipulate tissue using a distal portion of the jaw members without causing tissue damage. Accordingly, in some embodiments the at least first thermal zone can be positioned at a distal end of the end effector, while in other embodiments the at least second thermal zone can be positioned at a distal end of the end effector.

The at least one opening formed in the electrode to divide it into a plurality of thermal zones can have a variety of shapes, sizes, and configurations. In some embodiments, the at least one opening formed in the electrode can include a slit extending along a longitudinal axis of the end effector. Such a slit can serve to thermally isolate adjacent portions of the electrode and aid in the creation of different thermal zones. A slit or other opening extending substantially parallel to a longitudinal axis of the end effector can create, for example, the laterally offset thermal zones described above that provide a variation in thermal conductivity in a medial-lateral direction.

In other embodiments, the at least one opening formed in the electrode can include a slit that is transverse to a longitudinal axis of the end effector. In other embodiments, a plurality of slits can be formed at varying locations so as to create a plurality of thermal zones that are nearly thermally isolated from one another. The plurality of thermal zones can still be coupled to one another by one or more bridge features, however, such that the electrode has a single continuous conductive surface through which to direct energy into tissue captured between the jaw members.

The at least one opening formed in the electrode can, in some embodiments, remain empty as an air-gap between the various portions of the electrode. In other embodiments, however, at least one of the plurality of electrical insulators can be disposed within the at least one opening formed in the electrode to separate the plurality of thermal zones of the electrode from one another. The presence of an electrical insulator within the at least one opening can prevent unintentional shorting between adjacent portions of the electrode by tissue clamped between the jaw members.

In certain embodiments, a temperature dependent selectively conductive material can be disposed within the at least one opening formed in the electrode. Such a material can be configured to conduct electricity through a first range of temperatures, and not conduct electricity through a second range of temperatures, thereby modulating the delivery of electrical energy into tissue through portions of the electrode based on temperature. In some embodiments, the temperature dependent selectively conductive material can be a Positive Temperature Coefficient (PTC) material that becomes more resistive, and therefore less conductive, as its temperature increases. In other embodiments, the temperature dependent selectively conductive material can be a Negative Temperature Coefficient (NTC) material that becomes less resistive, and therefore more conductive, as its temperature increases.

In another aspect, a surgical end effector can include first and second jaw members movable relative to one another between an open position and a closed position to clamp tissue between tissue facing surfaces thereof, as well as an electrode having a single continuous conductive surface. The electrode can be coupled to the tissue facing surface of the first jaw member such that the electrode contacts tissue clamped between the first and second jaw members when in the closed position. The end effector can further include at least one thermal insulator disposed between the electrode and the tissue facing surface of the first jaw member, and at least one thermal conductor disposed between the at least one thermal insulator and the tissue facing surface of the first jaw member. A thickness of the at least one thermal insulator and a thickness of the at least one thermal conductor can vary along a portion of the end effector to produce at least a first thermal zone having a first thermal conductivity and a second thermal zone having a second thermal conductivity that is higher than the first thermal conductivity.

Similar to the end effector described above, a number of different variations and additional features are possible. For example, in some embodiments the thickness of the at least one thermal insulator can decrease linearly from a proximal end of the end effector to a distal end of the end effector. In other embodiments, the thickness of the at least one thermal conductor can increase linearly from the proximal end of the end effector to the distal end of the end effector.

In other embodiments, the thickness of the at least one thermal insulator can decrease in at least one step from a proximal end of the end effector to the distal end of the end effector. Conversely, the thickness of the at least one thermal conductor can increase in at least one step from the proximal end of the end effector to the distal end of the end effector. Such variation can have an effect of increasing the thermal conductivity (and therefore decreasing the temperature during operation) at a distal end of the device. In other embodiments, however, it can be desirable to invert this variation such that the thickness of the at least one thermal insulator increases from the proximal end of the end effector to the distal end of the end effector, and the variation can occur linearly, in one or more steps, or in other configurations (e.g., curved profiles, etc.).

In some embodiments, a sum of the thickness of the at least one thermal insulator and the thickness of the at least one thermal conductor can remain constant along the portion of the end effector, and the thickness of the at least one thermal insulator and the thickness of the at least one thermal conductor can vary inversely along the portion of the end effector. Such variation can, again, occur linearly, in one or more steps, or in other configurations (e.g., curved profiles, etc.).

The thickness of the at least one thermal insulator and/or the at least one thermal conductor can vary along any of a variety of portions of the end effector. For example, in some embodiments the portion can be defined by a longitudinal axis extending from a proximal end of the end effector to a distal end thereof. In other embodiments, however, the portion can be defined by an axis extending transverse to a longitudinal axis of the end effector (e.g., a medial-lateral axis of the end effector). Still further, in certain embodiments the portion can be defined by a three-dimensional shape, such as a curved central axis of a structure (e.g., a curved electrode, etc.). In such an embodiment, for example, variation in thickness can be inconsistent when viewed along a longitudinal axis of the end effector, but can be consistent along the three-dimensional shape.

In another aspect, a method for controlling temperature in an electrosurgical instrument can include positioning an end effector having first and second jaw members such that tissue is disposed within a gap between the first and second jaw members. The method can further include moving the first and second jaw members relative to one another to capture the tissue disposed within the gap. The method can also include delivering energy at different temperatures to the captured tissue across a length of the end effector through an electrode having a single continuous conductive surface that is coupled to at least one of the first and second jaw members.

In some embodiments, delivering energy at different temperatures to the captured tissue can occur by way of multiple thermal zones being formed across the length of the end effector. The multiple thermal zones can be formed in any variety of shapes, sizes, and orientations. In certain embodiments, for example, the thermal zones can include at least a first thermal zone and a second thermal zone extending along a longitudinal axis of the end effector with the second thermal zone being positioned laterally of the first thermal zone. In certain embodiments, the second thermal zone can have a lower temperature than the first thermal zone, while in other embodiments the second thermal zone can have a higher temperature than the first thermal zone. Arranging the thermal zones in this manner can create the medial-lateral variation in temperature that is discussed above (e.g., the creation of cooler thermal zones in lateral portions of the electrode and hotter thermal zones in medial portions of the electrode, or vice versa).

In other embodiments, delivering energy at different temperature to the captured tissue can occur by way of multiple thermal zones being formed across the length of the end effector such that the thermal zones include at least a first thermal zone and a second thermal zone extending along a longitudinal axis of the end effector with the second thermal zone being positioned distally of the first thermal zone and having a lower temperature than the first thermal zone. Further, in certain embodiments the second thermal zone can be positioned at a distal end of the end effector. In other embodiments, however, the second thermal zone can be positioned proximally of the first thermal zone, and the first thermal zone can be positioned at the distal end of the end effector.

As noted above, any of the additional features or variations described above can be applied to any particular aspect or embodiment of the invention in a number of different combinations; the absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which:

FIG. 3 is a perspective view of an alternative embodiment of an end effector and lower jaw electrode of an electrosurgical instrument;

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

The present invention is generally directed to surgical instruments and methods that are used in tissue cutting and sealing operations. Such operations can be particularly useful for, e.g., permanently sealing blood vessels in vessel transection procedures, welding organ margins in resection procedures, welding other anatomic ducts where permanent closure is required, and also for performing vessel anastomosis, vessel closure, or other procedures that join together anatomic structures or portions thereof. The devices and methods described herein employ multiple thermal zones of varying temperatures and/or thermal conductivities to optimally manage thermal energy and efficiently create tissue seals or welds. Providing multiple thermal zones over the area of an electrode can allow for the concentration of high temperatures where they are often most desirable (e.g., immediately adjacent to a tissue transection site), while simultaneously allowing thermal energy to be conducted or wicked away from areas where it is not often desirable (e.g., in neighboring tissue removed from the transection site).

Figure 1:
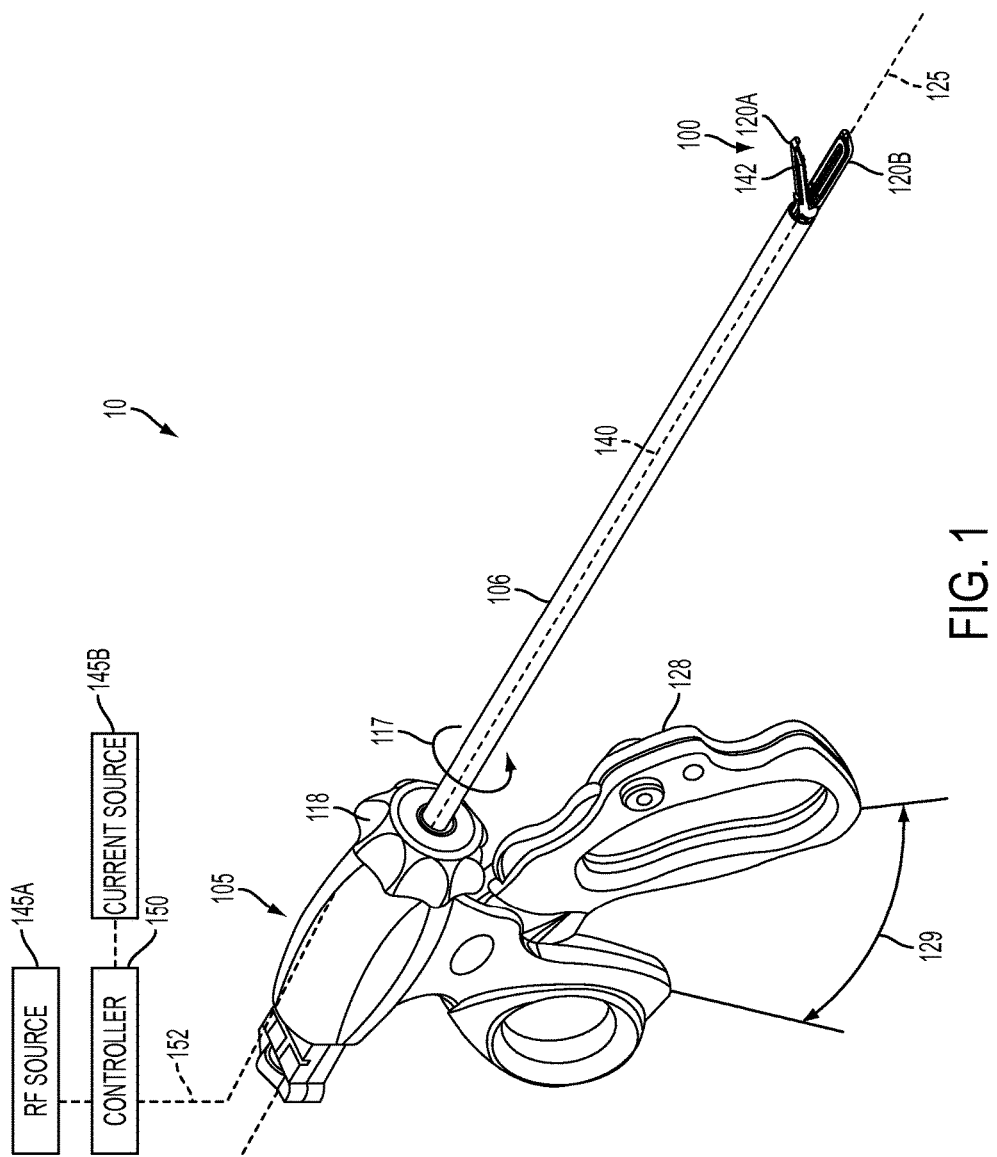
FIG. 1 is a perspective view of one embodiment of an electrosurgical instrument for cutting and sealing tissue.

FIG. 1 shows an electrosurgical instrument 10 according to an embodiment of the invention. The electrosurgical instrument 10 can include a proximal handle end 105, a distal end effector 100, and an introducer or shaft member 106 disposed in-between. The end effector 100 can include a set of movable jaw members having a straight or curved shape and including a first, or upper, jaw member 120A and a second, or lower, jaw member 120B. The first jaw member 120A and the second jaw member 120B can each include an elongate channel 142 disposed outwardly along their respective middle portions. The first jaw member 120A and the second jaw member 120B can be coupled to a first electrical source or RF source 145A, a second electrical source 145B, and a controller 150 through electrical leads in cable 152. The controller 150 can be used to separately activate the first electrical source 145A and the second electrical source 145B.

As seen in FIG. 1, the handle end 105 can include a lever arm 128 which can be pulled along a path 129. The lever arm 128 can be coupled to a translatable, reciprocating member 140 disposed within the introducer or shaft member 106. The handle can be any type of pistol-grip or other type of handle known in the art that is configured to carry actuator levers, triggers, or sliders for actuating the first jaw member 120A and the second jaw member 120B. The introducer or shaft member 106 can have a cylindrical, rectangular, or other cross-section and can include a thin-wall tubular sleeve that extends from the handle 105 to the end effector 100. The introducer or shaft member 106 can have a bore extending therethrough for carrying various actuator mechanisms for moving, e.g., the translatable, reciprocating member 140 or the first and second jaw members 120A, 120B, as well as electrical leads for delivery of electrical energy to electrosurgical components of the end effector 100.

The end effector 100 can be adapted for capturing, welding/sealing, and transecting tissue. The first jaw member 120A and the second jaw member 120B can close to thereby capture or engage tissue between tissue facing surfaces thereof about a longitudinal axis 125 of the end effector. The first jaw member 120A and the second jaw member 120B can also apply compression to the tissue. The introducer or shaft member 106, along with the first jaw member 120A and the second jaw member 120B, can be rotated a full 360 degrees, as shown by arrow 117, relative to the handle 105 using, for example, a rotary controller 118. The first jaw member 120A and the second jaw member 120B can remain movable/operable while rotated to any angle. Further, the first jaw member 120A and the second jaw member 120B can be coupled to a first electrical source 145A, a second electrical source 145B, and a controller 150 through electrical leads in cable 152 to function as paired bi-polar electrodes with a positive polarity (+) and a negative polarity (−).

Figure 1A:
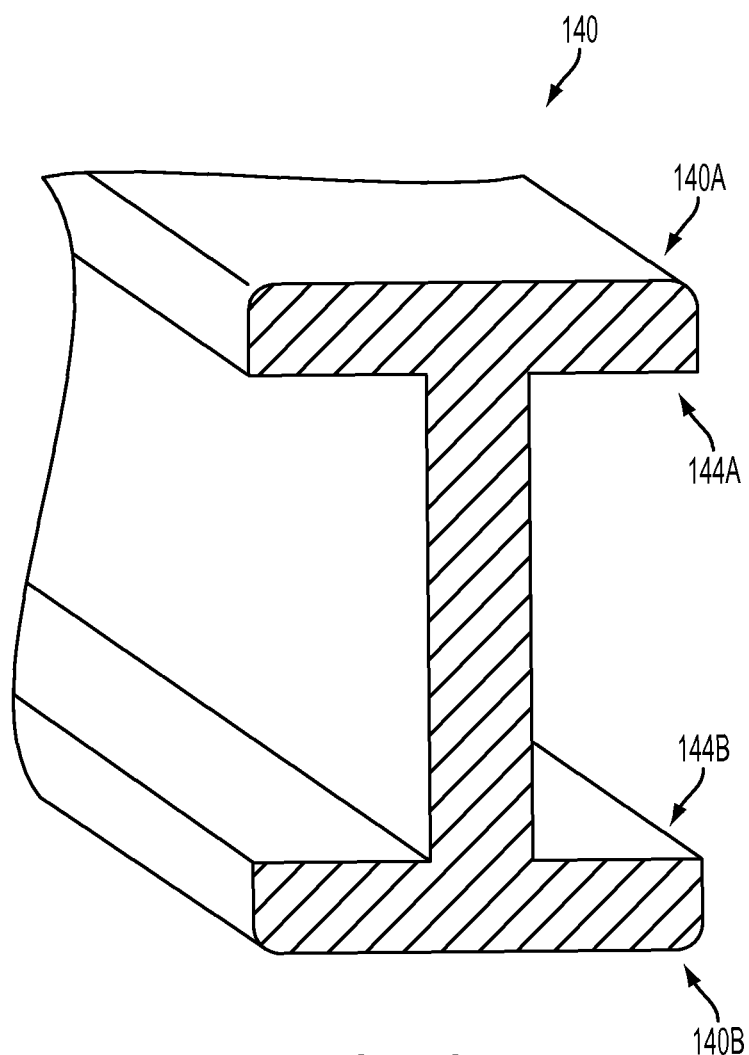
FIG. 1A is a perspective view of one embodiment of a translatable member of the electrosurgical instrument shown in FIG. 1.

FIG. 1A shows a portion of a translatable, reciprocating member or reciprocating "I-beam" member 140. The lever arm 128 of handle 105 can be adapted to actuate the translatable member 140, which can also function as a jaw-member-closing mechanism. For example, the translatable member 140 can be urged distally as the lever arm 128 is pulled proximally along the path 129. The distal end of the translatable member 140 can include a flanged "I"-beam configured to slide within channels 142 in the first and second jaw members 120A and 120B. The translatable member 140 can slide within the channels 142 to move the first jaw member 120A and the second jaw member 120B between an open and a closed configuration. The distal end of the translatable member 140 can include an upper flange 140A and a lower flange 140B. The flanges 140A and 140B can respectively define inner cam surfaces 144A and 144B for engaging outward facing surfaces of the first jaw member 120A and the second jaw member 120B, respectively. The movement of the first jaw member 120A and the second jaw member 120B between the open and closed positions can apply high compressive forces to tissue disposed therebetween using the cam mechanisms of the reciprocating "I-beam" member 140. Various cam mechanisms are known in the art and can be employed.

A person skilled in the art will recognize other non-limiting examples of features that can be incorporated with the handle portion 2 to assist in manipulating or otherwise operating the device include: (1) an articulation lever for articulating the end effector 100; (2) a firing lockout assembly to prevent the translatable member from being actuated at an undesirable time; and (3) an emergency return button to retract the translatable member before its stroke is completed, for instance in a case where completing the stroke may cause tissue to be undesirably transected. Although features such as an articulation lever, a firing lockout assembly, and an emergency return button are not explicitly illustrated in the device 10, a person skilled in the art will recognize a variety of configurations for each feature that can be incorporated into the handle portion 105 and/or other portions of the device 10 without departing from the spirit of the present disclosure.

Further information on electrosurgical end effectors, jaw closure mechanisms, and electrosurgical energy-delivery surfaces are described in the following U.S. patents, all of which are incorporated by reference in their entirety and made a part of this specification: U.S. Pat. Nos. 7,381,209; 7,354,400; 7,311,709; 7,220,951; 7,189,233; 7,186,253; 7,169,147; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176, as well as U.S. Pat. Pub. Nos. 2010/0036370 and 2009/0076506. The various embodiments disclosed in these references can be utilized and combined with the devices and methods described herein.

As mentioned above, efficient performance of tissue sealing surgical instruments depends on careful management of thermal energy developed in the tissue during operation. Sufficient heat must be created to produce the desired tissue seal or weld, but care must be taken to not cause collateral damage to adjacent tissue. Thermal transfer of energy out of the tissue and into the jaws of a device can affect the performance of the device. For example, a device with a high level of thermal conductivity can easily prevent overheating of tissue that can lead to collateral tissue damage because excess heat can be wicked or conducted away by the jaw members of the device. However, the temperature developed at the tissue sealing site can also be decreased, which can significantly increase the time required to form a tissue seal or weld. Conversely, if the level of thermal conductivity is very low, heat developed in the device electrode(s) or tissue will not be readily conducted into the jaw members of the device and will therefore remain concentrated in the tissue and electrode. This can form tissue seals more quickly, but can also lead to the problems described above associated with overheating the treated and surrounding tissue.

The devices and methods described herein provide for optimal management of thermal energy in an electrosurgical device through the use of multiple thermal zones over the area of an electrosurgical device electrode or other active element. More particularly, the electrode (or other active element) can be divided into a plurality of thermal zones, some having the ability to achieve higher temperatures and others having the ability to achieve lower temperatures. The number, shape, size, and orientation of the thermal zones can be selected so as to optimally manage thermal energy developed in the tissue during a sealing operation. For example, thermal zones of higher temperature can be created immediately adjacent to a tissue transection site, as higher temperatures are typically desired at this location to create a tissue seal quickly. Conversely, thermal zones of lower temperature can be created adjacent to the higher temperature thermal zones, e.g., at the outer portions of an electrode, as reducing the temperature in these areas can prevent lateral thermal spread that can damage adjacent tissue that is outside of the jaws and not in contact with the electrode. Further, excess thermal energy in the higher temperature thermal zones can flow into the lower temperature thermal zones, thereby preventing problems associated with overheating, as described above.

The methods and devices described herein generally provide thermal zones of varying temperatures by varying the thermal conductivity of electrical insulators that are disposed between the jaw members and electrode(s) of the device. For example, placing an electrical insulator having a high thermal conductivity under a portion of an electrode can create a thermal zone of lower temperature due to an increased amount of thermal energy transferring into the jaw member via the electrical insulator. Conversely, placing an electrical insulator of low thermal conductivity under a portion of an electrode can create a thermal zone of higher temperature due to thermal energy not being able to transfer efficiently into the jaw member through the electrical insulator. As is illustrated in the various embodiments described herein, varying the thermal conductivity of an electrical insulator, or a portion of an end effector generally, can include utilizing materials that have differing coefficients of thermal conductivity (e.g., substances having different material properties with regard to conducting heat), shaping, arranging, or otherwise configuring a single material to exhibit different levels of thermal conductivity (e.g., using more of a material in one location than another, etc.), or any combination of these techniques.

The electrodes of the devices described herein can also include features designed to achieve substantial thermal isolation of various regions of an electrode from one another. For example, an electrode can include at least one opening formed therein, e.g., a slit, gap, through-hole, channel, etc., that can serve as a thermal break that prevents the transfer of thermal energy between adjacent sections of an electrode. The openings formed in the electrode to prevent thermal energy transfer can be selectively created such that at least one bridging portion remains to electrically connect the various sections of the electrode. The electrode can therefore maintain a single continuous conductive surface. This can be advantageous because the use of multiple electrodes in an end effector can increase the device's complexity and cost (e.g., from the increased electrical connections, driving circuitry, manufacturing steps, etc.).

Figure 2A:
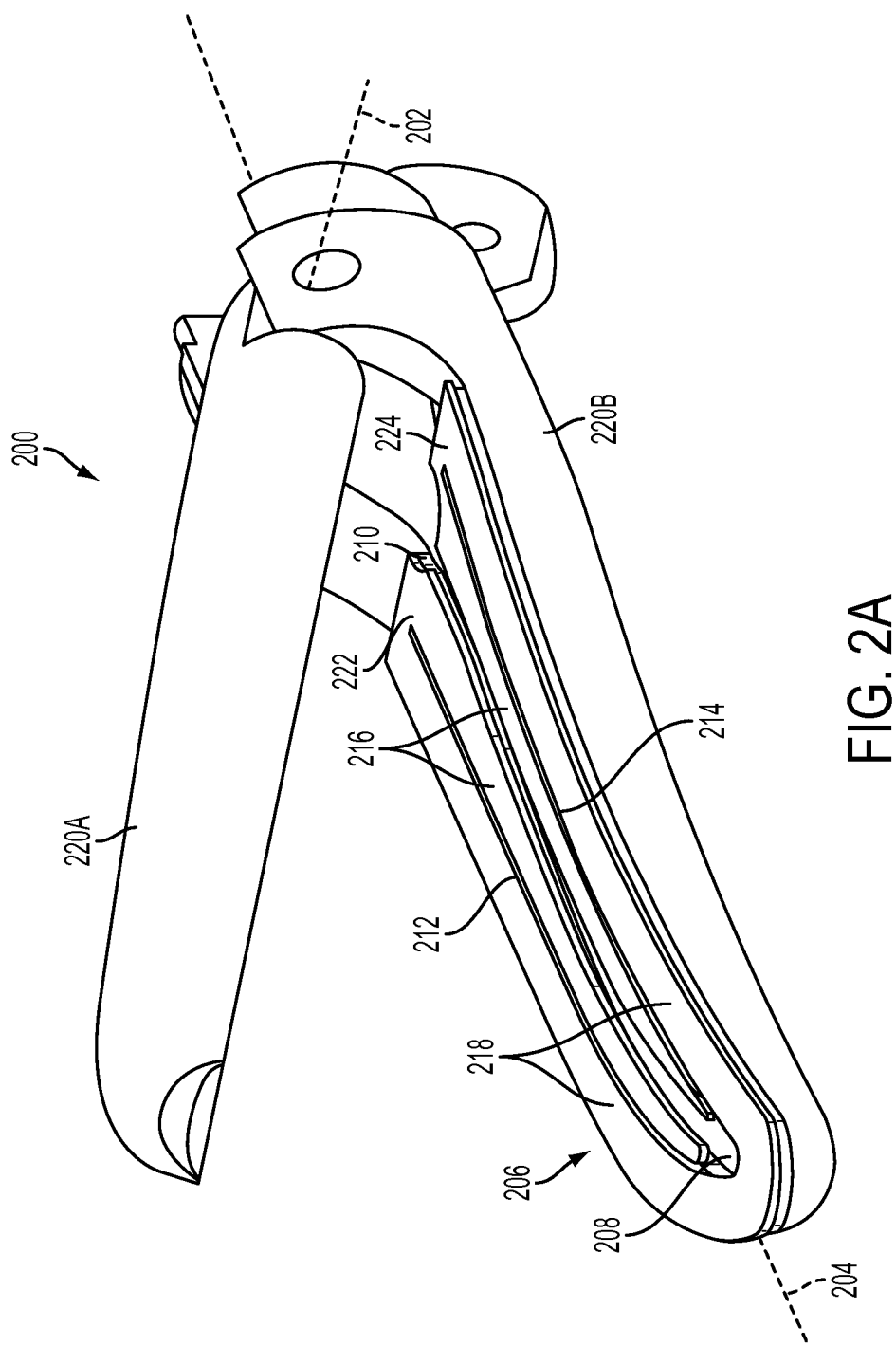
FIG. 2A is a perspective view of one embodiment of an end effector and lower jaw electrode of an electrosurgical instrument.
Figure 2B:
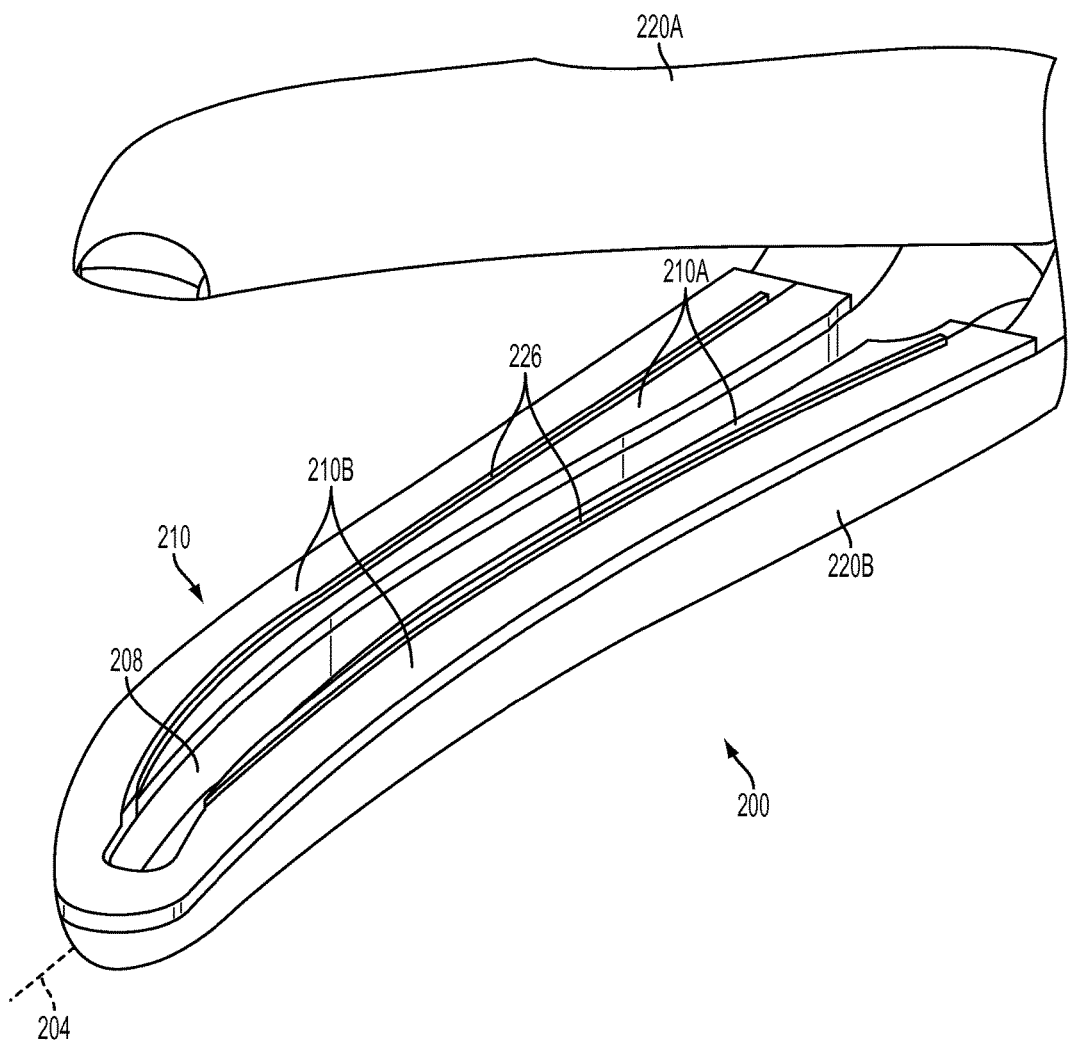
FIG. 2B is an alternative view of the end effector of FIG. 2A and electrical insulators that separate the lower jaw electrode from the lower jaw.

FIGS. 2A and 2B illustrate one embodiment of an end effector according to the teachings of the present invention. Similar to the end effector 100 described above, the end effector 200 can be configured to couple to a shaft 106 coupled to a handle portion 105 of an electrosurgical device 10. The end effector 200 can include first and second jaw members 220A, 220B that are movable relative to one another between an open position (illustrated) and a closed position (not shown) to clamp tissue disposed between tissue facing surfaces of the first and second jaw members (e.g., tissue disposed between a lower surface of the jaw member 220A and an upper surface of the jaw member 220B). In the illustrated embodiment, the first and second jaw members 220A, 220B are configured to pivot relative to one another about the axis 202.

The jaw members 220A, 220B can have an elongate shape extending along a longitudinal axis 204 of the end effector 200. The end effector 200 can have any of a variety of sizes configured for insertion into a patient's body during an open or minimally invasive surgical procedure. Further, the first and second jaw members 220A, 220B can be formed from any of a variety of biocompatible materials known in the art. Examples include, but are not limited to, stainless steel and titanium.

At least one of the first and second jaw members 220A, 220B can have an electrode 206 disposed thereon and configured to contact tissue clamped between the first and second jaw members when in the closed position. The electrode 206 can be configured to deliver energy into the tissue to create a tissue seal or weld. In some embodiments, the electrode 206 can be an active electrode disposed on jaw member 220B, and the conductive material of the jaw member 220A and shaft member 106 can function as a return electrode. Accordingly, there need not be an electrode similarly disposed on the jaw member 220A. Alternatively, in other embodiments a mirrored configuration can be created on the jaw member 220A.

The electrode 206 can be shaped to cover substantially all of a tissue-facing surface of the jaw member 220B and, similar to the jaw member 220B itself, can include a central channel 208 to allow a translatable member 140 to advance and transect the tissue clamped between the jaw members. Further, one or more electrical insulators 210 can be disposed between the electrode 206 and the jaw member 220B to prevent an electrical short between the components.

As mentioned above, a plurality of thermal zones can be created over the surface area of the electrode 206 via the combination of one or more openings formed in the electrode and the use of electrical insulators having different thermal conductivities. In the embodiment shown in FIGS. 2A and 2B, for example, first and second longitudinal slits 212, 214 are formed in the electrode 206. The longitudinal slits 212, 214 create thermal breaks in the electrode that prevent the transfer of thermal energy between the inner, or medial, portions 216 of the electrode and the outer, or lateral, portions 218 of the electrode. The longitudinal slits 212, 214 can be effective to substantially thermally isolate adjacent portions of the electrode from one another, but the electrode can have a single continuous electrically conductive surface due to bridging portions 222, 224 that connect the inner and outer portions 216, 218 of the electrode. The bridging portions 222, 224 can be formed by selectively creating the slits 212, 214 or other openings such that connecting or bridging portions remain, or they can be created by coupling a wire or other conductor between adjacent portions of an electrode to facilitate electrical connectivity therebetween. In still other embodiments, a temperature dependent selectively conductive material can be used to form bridging portions 222, 224, as discussed in more detail below.

The longitudinal slits 212, 214 or other openings formed in the electrode 206 can create thermal isolation between the various portions 216, 218 of the electrode, and the thermally isolated portions can be made into thermal zones of varying temperature by varying the thermal conductivity of the one or more electrical insulators 210 upon which the portions of the electrode sit. FIG. 2B illustrates the end effector 200 of FIG. 2A with the electrode 206 hidden from view to illustrate the insulators 210 disposed between the jaw 220B and the electrode 206. As shown in the figure, the inner, or medial, portions 216 of the electrode are coupled to a first electrical insulator 210A and the outer, or lateral, portions 218 of the electrode are coupled to a second electrical insulator 210B. The first and second electrical insulators 210A, 210B can have different levels of thermal conductivity (i.e., different coefficients of thermal conductivity) such that the portions 216, 218 of the electrode connected thereto will define different thermal zones during operation of the device.

Also shown in FIG. 2B is a ridge 226 formed on the electrical insulator 210B that is configured to be disposed within the slits 212, 214 formed in the electrode 206, and can be disposed proud of the surface of the electrode 206. In certain embodiments, the slits, channels, gaps, or other openings formed in the electrode can be left as air gaps, as such an opening can create the desired thermal break between adjacent portions of the electrode. However, in use tissue may become compressed in the air gap and may create a path for conduction between the adjacent portions of the electrode. The ridge 226 can provide further assurance of electrical and/or thermal insulation between the adjacent portions of the electrode, thereby improving performance.

The electrical insulators 210A, 210B can be selected so as to create any desired arrangement of thermal zones within the end effector. For example, in some embodiments the first electrical insulator 210A can have a lower thermal conductivity than the second electrical insulator 210B such that a thermal zone of higher temperature is created in the medial, or inner, portions 216 of the end effector near the central channel 208 where tissue is transected. This can allow the tissue contacting the inner portions 216 of the electrode to heat more rapidly and to a higher temperature to create a good quality seal. The higher thermal conductivity of the second electrical insulator 210B can conversely create a thermal zone of lower temperature in the outer, or lateral, portions 218 of the electrode. This can allow the tissue contacting the outer portions 218 of the electrode to heat more slowly, and excess thermal energy can be wicked or conducted into the jaw member 220B so as to minimize thermal energy transfer into surrounding tissue outside of the jaw members 220A, 220B.

In an alternative embodiment, however, the first electrical insulator 210A can have a higher thermal conductivity than the second electrical insulator 210B, effectively reversing the configuration described above. Such an arrangement can create a thermal zone of lower temperature in the medial, or inner, portions 216 of the end effector and a thermal zone of higher temperature in the outer, or lateral, portions 218 of the end effector. Despite locating the thermal zone of higher temperature farther away from the tissue transaction site, such a configuration can actually decrease the amount of thermal spread to tissue outside the jaws 220A, 220B. This is possible because the impedance of tissue can increase as its temperature rises. Accordingly, more rapidly heating tissue at the outer edges of the electrode 206 can create a barrier region having a high level of impedance that can prevent the transmission of electrical current into tissue outside the jaws 220A, 220B. Rather, any current delivered from the electrode 206 can be more effectively contained within the tissue trapped between the jaws 220A, 220B. Such a configuration can be particularly advantageous in instruments having large-area opposed electrodes, as thermal spread can occur more easily with these devices.

The creation of longitudinally extending thermal zones having varying temperature or thermal conductivity in the medial-lateral direction (i.e., perpendicular to the longitudinal axis 204 of the end effector) is just one embodiment of a possible arrangement for thermal zones in an end effector. Any combination of slits or other openings can be formed in the electrode 206, and can be combined with the placement of any combination of electrical insulators having different thermal conductivities, to create any combination of thermal zones during operation of the device. FIG. 3 illustrates an alternative embodiment of an end effector 300 similar to the end effector 200, but including additional slits 302 formed in the electrode 306 that are transverse to the longitudinal axis 304 of the end effector. The addition of such slits, in combination with the placement of corresponding electrical insulators 310 of varying thermal conductivities, can create a different pattern of thermal zones over the area of the electrode 306, while maintaining a single continuous conductive surface.

For example, the use of transverse slits 302 alone, in combination with alternating electrical insulators of higher and lower thermal conductivity, can create thermal zones of higher and lower temperature that alternate along the longitudinal axis 304 of the end effector 300. In still other embodiments, it can be desirable to create either a hotter or cooler thermal zone at a distal end of the end effector, depending on the intended use. For example, creating a thermal zone of higher temperature at a distal end of the device can allow a surgeon or other user to perform precise touch-up operations after transecting and sealing tissue. In other embodiments, however, a surgeon or user can use a thermal zone of lower temperature at a distal end of the end effector to grasp tissue without causing damage thereto. Either thermal zone can be created by using, for example, a transverse slit or other opening formed in a distal portion of the electrode 206, 306, in combination with either an electrical insulator of high thermal conductivity (for a lower temperature thermal zone) or low thermal conductivity (for a higher temperature thermal zone). Such a configuration at a distal end of the device can be combined with longitudinal slits, such as slits 212, 214, transverse slits, such as slits 302, or any other combination of openings. By way of non-limiting example, in one embodiment an end effector can have longitudinally-extending thermal zones of lower temperature disposed laterally of longitudinally-extending thermal zones of higher temperature, and these zones can abut against a thermal zone of either higher or lower temperature formed at a distal end of the device. In any of these embodiments, the electrode 306 can retain a single continuous conductive surface despite the presence of various openings formed in the electrode and insulators coupled thereto that serve to thermally isolate portions of the electrode.

In some embodiments, it can be possible to create a plurality of thermal zones over the area of an electrode by varying a thickness of a thermal insulator (or insulators) and a thickness of a thermal conductor (or thermal conductors) disposed between an electrode and a jaw member of an end effector. Further, in certain embodiments varying the ratio of the thermal insulator and thermal conductor thicknesses can create thermal zones without the need to form openings in the electrode to thermally isolate portions thereof. In still other embodiments, varying thicknesses of thermal insulators and conductors in contact with an electrode can be used with any configuration of openings formed in the electrode (or electrodes) to create desired thermal zones.

Figure 4:
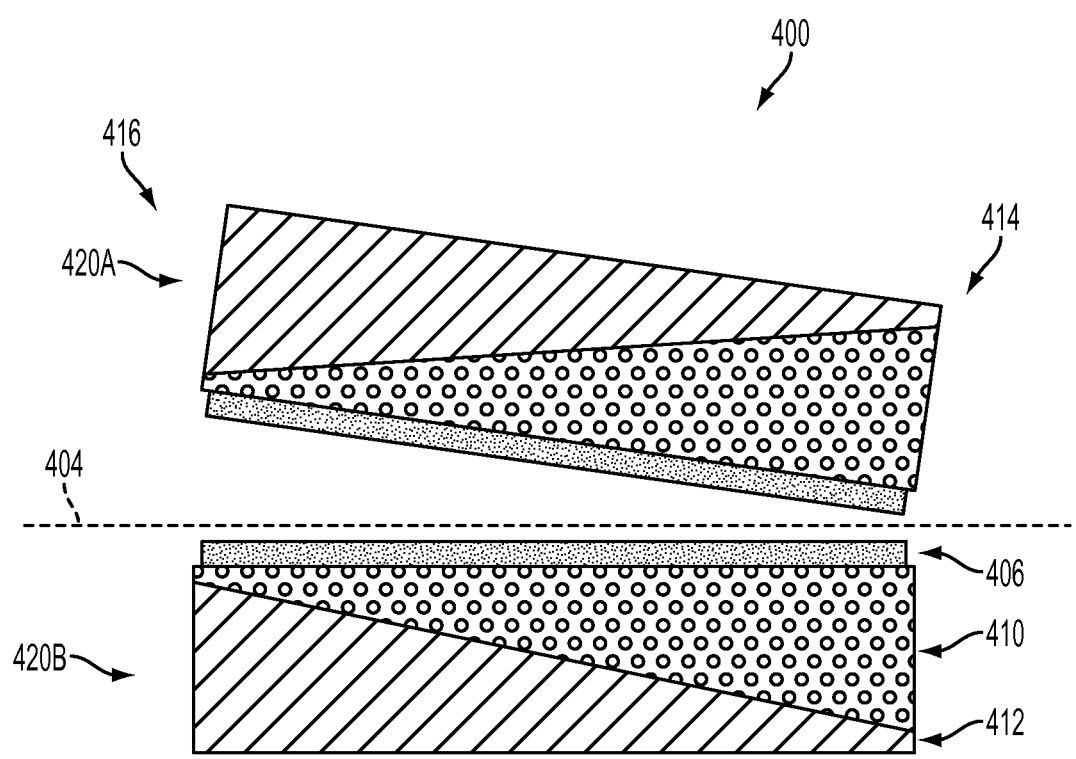
FIG. 4 is a side cross-sectional view of one embodiment of an end effector of an electrosurgical instrument.

FIG. 4 illustrates a side cross-sectional view of one such embodiment of an end effector 400 having a first jaw member 420A and a second jaw member 420B. The second jaw member 420B has an electrode 406 having a single continuous conductive surface coupled thereto via a thermal insulator 410 and a thermal conductor 412. As shown in the figure, a thickness of the thermal insulator 410 and a thickness of the thermal conductor 412 can vary along a length of the end effector (i.e., vary along a longitudinal axis 404 of the end effector, though variation along other portions of an end effector 400 are also possible, as described in more detail below). The varying thickness of the thermal insulator 410, alone or in combination with the varying thickness of the thermal conductor 412, can create different thermal zones in the electrode 406 during operation.

The thicknesses of the thermal insulator 410 and the thermal conductor 412 can be varied in a number of different manners. For example, the embodiment shown in FIG. 4 illustrates a linear decrease in the thickness of the thermal insulator 410 from a proximal end 414 of the end effector 400 to a distal end 416 thereof. Conversely, a thickness of the thermal conductor 412 increases linearly from the proximal end 414 of the end effector 400 to the distal end 416 thereof. Such an arrangement can create a thermal zone of higher temperature at a proximal end 414 of the electrode 406 and a thermal zone of lower temperature at the distal end 416 of the electrode, with a gradual transition between the two moving from the proximal to distal end of the electrode. Any point along the length of the end effector can represent its own distinct thermal zone based on the level of thermal conductivity at that discrete location. A lower temperature thermal zone at the distal end 416 can be helpful, for example, when grasping tissue immediately after sealing, as residual thermal energy can be directed away from a distal portion of the electrode 406.

Other variations are possible to create any desired pattern of thermal zones during operation and immediately thereafter as the device is cooling. For example, the arrangement shown in FIG. 4 can be inverted such that the thickness of the thermal insulator increases linearly from the proximal end to the distal end of the end effector (and the thickness of the thermal conductor likewise linearly decreases) to create a thermal zone of elevated temperature at a distal end of the end effector.

In still other embodiments, the configuration shown in FIG. 4 can be adapted to create medial-lateral temperature variations similar to those described above in connection with FIGS. 2A and 2B. This can be accomplished by varying a thickness of a thermal insulator or conductor in a direction transverse to a longitudinal axis of the end effector (e.g., from an inner portion of an electrode to an outer portion thereof). Further, in some embodiments the variation in thickness can extend around a three-dimensional shape, e.g., the curve of the distal end of the end effector, such that there is no consistency when viewed along a longitudinal or medial-lateral axis, but only when viewed along the three-dimensional shape.

Figure 4A:
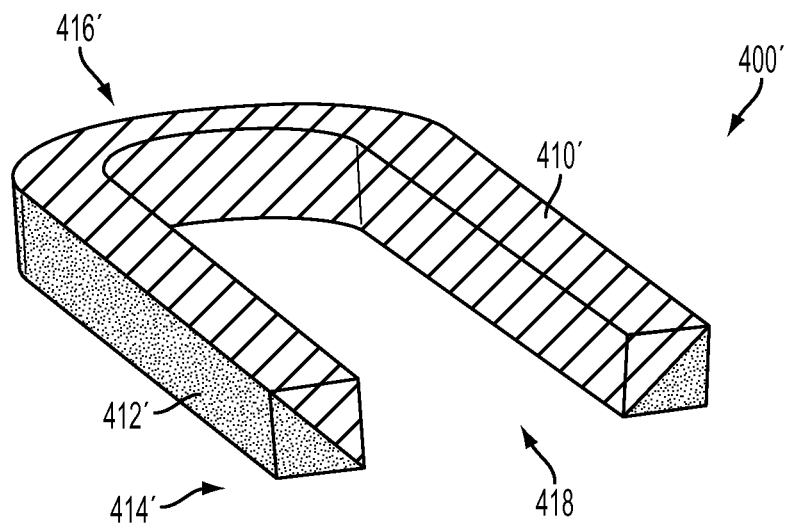
FIG. 4A is a perspective view of one embodiment of an end effector of an electrosurgical instrument.
Figure 4B:
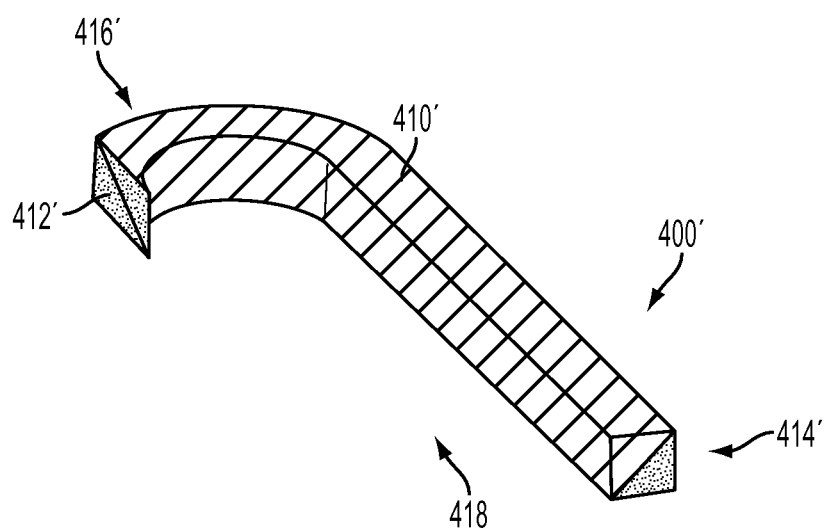
FIG. 4B is an alternative perspective view of the end effector of FIG. 4A.

FIGS. 4A and 4B illustrate one embodiment of such a configuration in which a thickness of a thermal insulator 410' and a thermal conductor 412' are varied in the medial-lateral direction of the electrode 406, as viewed from a proximal end 414' of the end effector 400'. The cross-sectional profile of the thermal insulator 410' and thermal conductor 412' shown at the proximal end 414' of the end effector 400' can be maintained throughout the U-shape of the distal end 416' of the end effector that can surround a central slot 418, similar to the slot 208 described above. As a result of the three-dimensional curved shape at the distal end 416' of the end effector 400', there would be no consistent cross-sectional shape when viewed along a longitudinal axis or medial-lateral axis of the end effector. However, there is a consistent cross-sectional shape extending along the three-dimensional shape of the insulator 410' and/or conductor 412' that sweep around the profile of the end effector 400'.

The configuration illustrated in FIGS. 4A and 4B can create a higher temperature thermal zone (i.e., lower conductivity) in a central portion of the end effector 400' that transitions to a lower temperature thermal zone (i.e., higher conductivity) in an outer portion of the end effector. As mentioned above, this arrangement can also be reversed to create a lower temperature thermal zone in the central portion and a higher temperature thermal zone in the outer portion of the end effector.

Figure 5:
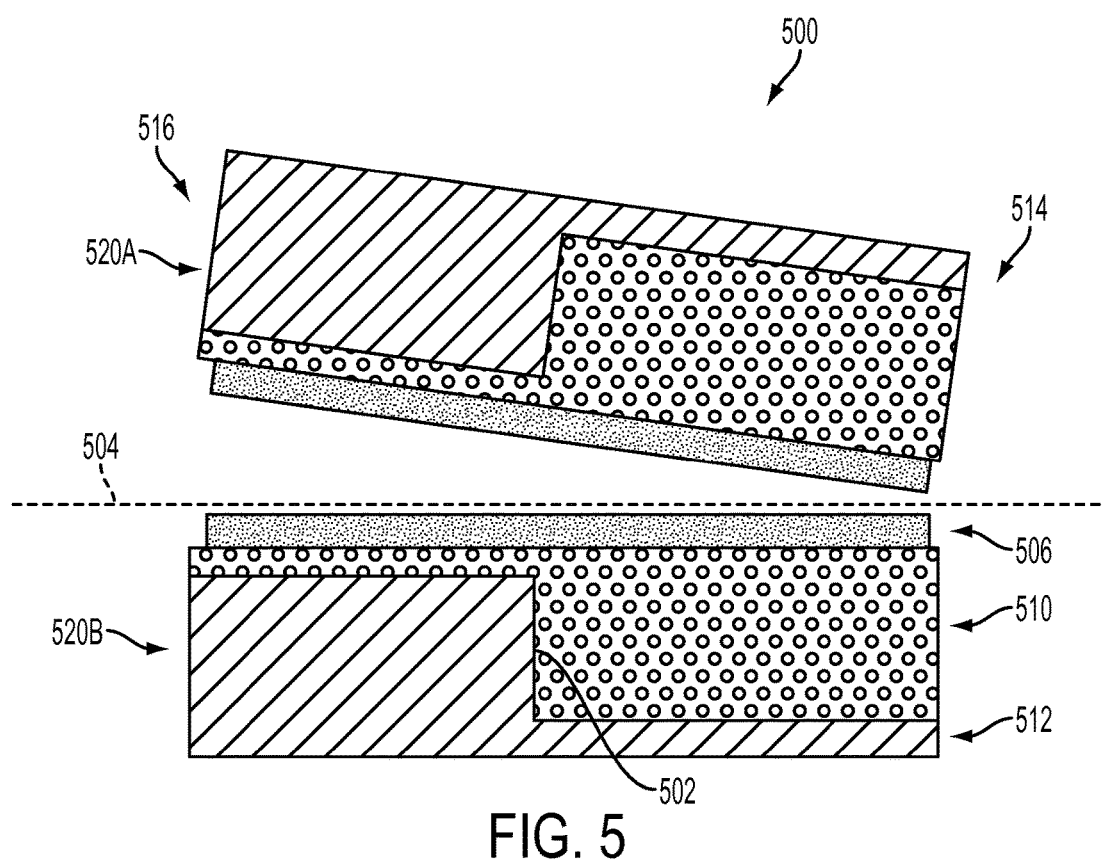
FIG. 5 is a side cross-sectional view of an alternative embodiment of an end effector of an electrosurgical instrument.

In addition, the gradual variation in temperature created by a linear increase in thickness (i.e., the blended division between the thermal zones of high and low temperature) can be substituted for other transitions, such as a stepped transition shown in an end effector 500 of FIG. 5. In such an embodiment, an electrode 506 having a single continuous conductive surface can be coupled to a jaw member 520B, and a thickness of a thermal insulator 510 and a thickness of a thermal conductor 512 can vary along a length of an end effector 500, similar to the embodiment illustrated in FIG. 4. However, this variation can occur in one or more steps 502, rather than via a linear increase or decrease. Varying the thicknesses of the insulator 510 and conductor 512 in this manner can create a thermal zone of elevated temperature proximally of the step 502, and a thermal zone of reduced temperature distally of the step. In still other embodiments, other variation profiles are possible, including various curves or repeating patterns of steps or gradations, such as a saw-tooth pattern of steps, or a sine wave curve pattern. Regardless of the particular pattern for varying the thicknesses of the thermal insulator and the thermal conductor, variation of the ratio of their thicknesses can create thermal zones of higher or lower temperatures during a tissue sealing operation, in accordance with the disclosures provided herein.

In the embodiments shown in FIGS. 4 and 5, a sum of the thicknesses of the thermal insulators 410, 510 and the thermal conductors 412, 512 remains constant along a length of the end effectors 400, 500, and the thicknesses of the two components vary inversely with one another. Such a configuration need not be present in every embodiment. Further, in some embodiments the thermal conductor can be the material of the jaw member 420B, 520B itself (e.g., stainless steel). In such an embodiment, a thickness of the jaw member 420B, 520B may or may not vary along its length, but a thickness of a thermal insulator can be varied to create different thermal zones during operation of the device.

Additionally, the arrangement shown for the jaw members 420B, 520B can be mirrored to the jaw members 420A, 520A in some embodiments, as shown in FIGS. 4 and 5. In other embodiments, however, an active electrode 406, 506 may be present on only one of the jaw members, and an opposing jaw member can be formed from a single material. In still other embodiments, an opposing jaw member can have a temperature dependent selectively conductive material formed thereon so as to become more or less conductive as the temperature increases. Embodiments employing these materials are discussed in more detail below.

The end effector 200 described above utilizes openings formed in an electrode 206 to achieve thermal isolation between portions thereof. Further, as shown in FIG. 2B, a portion of an electrical insulator, i.e., the ridge 226, can be configured to be disposed within any opening formed in the electrode to prevent thermal or electrical conduction across the opening from, for example, tissue becoming disposed in the opening. In other embodiments, a temperature dependent selectively conductive material can be disposed within a gap or opening between portions of an electrode, or between separate electrodes, to selectively couple them together. In still other embodiments, a temperature dependent selectively conductive material can be used to replace, for example, the bridging portions 222, 224 of the electrode 206 shown in FIG. 2, thereby providing for dynamic activation of selected portions of an electrode.

Figure 6:
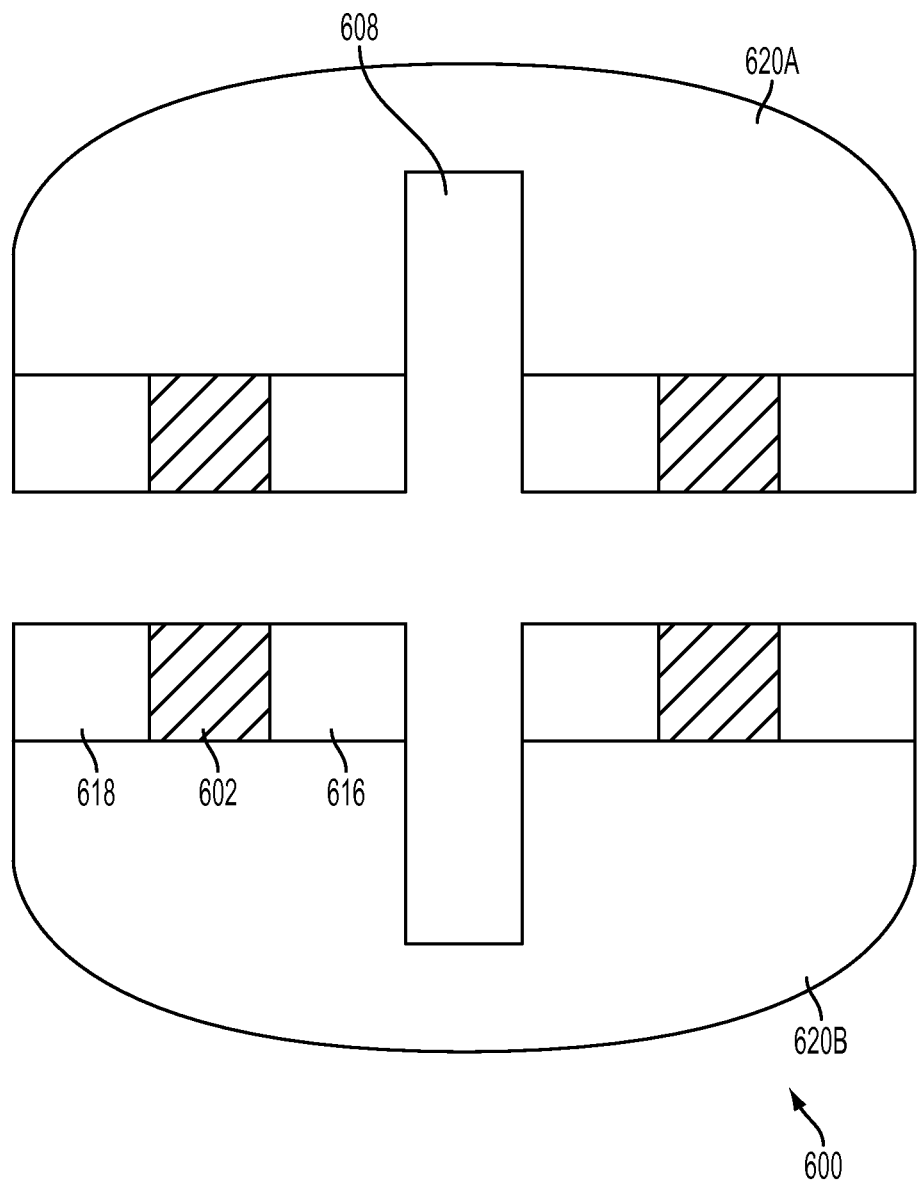
FIG. 6 is a front cross-sectional view of one embodiment of an end effector of an electrosurgical instrument that includes electrodes with temperature dependent selectively conductive regions.
Figure 7:
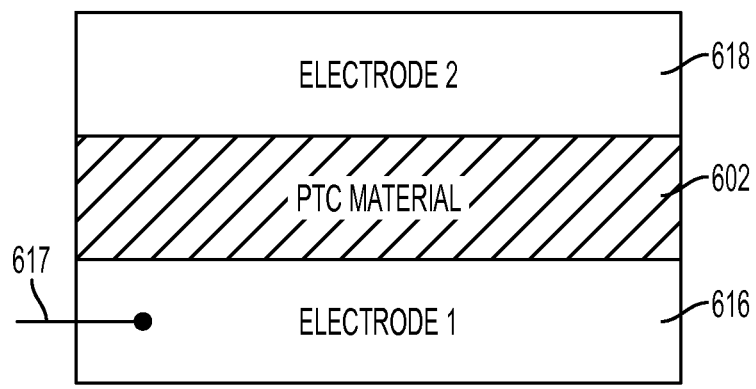
FIG. 7 is a top view of an electrode of the end effector of FIG. 6.

FIGS. 6 and 7 illustrate one embodiment in which an end effector having first and second jaw members 620A, 620B includes an inner electrode 616 that is coupled to an electrical signal generator via connection 617 and selectively coupled to an outer electrode 618 via a temperature dependent selectively conductive material 602. The temperature dependent selectively conductive material 602 can be, for example, either a Positive Temperature Coefficient (PTC) material or a Negative Temperature Coefficient (NTC) material. In a PTC material, electrical resistivity can increase as temperature increases. This can result in a PTC material conducting electricity at lower temperatures and not conducting (or not conducting as well) at higher temperatures. Conversely, in an NTC material, electrical resistivity can decrease as temperature increases, which can result in an NTC material conducting at higher temperatures and not conducting at lower temperatures.

In the embodiment shown in FIGS. 6 and 7, for example, the temperature dependent selectively conductive material 602 can be a PTC material that conducts electricity at lower temperatures and does not conduct electricity at higher temperatures. Accordingly, both the inner electrode 616 and the outer electrode 618 can be heated during an initial portion of a sealing operation when the temperature is low. As the temperature in the PTC material 602 increases, however, so does its electrical resistivity, until electrical conduction is substantially or completely halted. At such a time, the outer electrode 618 can function more as a heat sink than source, which can prevent lateral thermal spread to tissue outside the jaw members 620A, 620B. Such an arrangement can allow the use of an electrode having a single continuous conductive surface that can be selectively activated due to the use of PTC material 602 for portions of the surface.

In other embodiments, however, an NTC material can be employed for the temperature dependent selectively conductive material 602. In such an embodiment, the smaller inner electrode 616 can be heated first to create a seal immediately adjacent to the channel 608 where tissue is transected by the translatable member 140, and the outer electrode 618 can be heated some time later after the NTC material increases in temperature. This arrangement can have the benefit of requiring less power to create a tissue seal or weld, as only the inner electrode 616 is initially active and smaller volume of tissue is initially treated.

Figure 8:
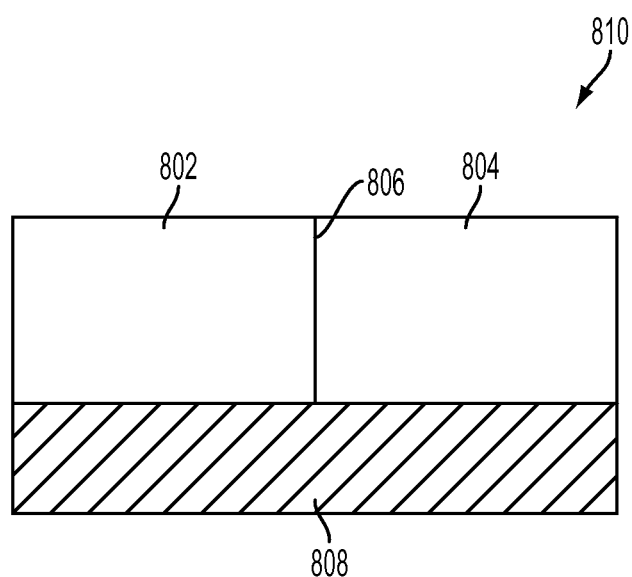
FIG. 8 is a front cross-sectional view of an alternative embodiment of an electrode that includes temperature dependent selectively conductive regions.

FIG. 8 illustrates an alternative embodiment for arranging an electrode including a temperature dependent selectively conductive material to dynamically adjust current flow based on temperature. In the illustrated configuration, a first electrode portion 802 (e.g., an inner or medially positioned portion) is positioned adjacent to a second electrode portion 804 (e.g., an outer or laterally positioned portion) and separated therefrom over at least a portion of the electrode by a thin electrical insulator 806. A temperature dependent selectively conductive material 808, such as a PTC or an NTC material, extends underneath the first and second electrode portions 802, 804. The temperature dependent selectively conductive material 808 can therefore selectively conduct electricity between the two electrode portions 802, 804 depending on the temperature of the material 808. Further, an upper surface 810 can be configured to contact tissue. As a result, the PTC or NTC material 808 can dynamically alter the path of current through any tissue contacting the first and second electrodes 802, 804, and such alteration can be based on temperature. The configuration of the electrode and arrangement of temperature dependent selectively conductive material shown in FIG. 8 can be, for example, provided on a single jaw member of an end effector, or can be mirrored across opposing jaw members, similar to the configuration shown in FIG. 6 on jaw members 620A, 620B.

Figure 9:
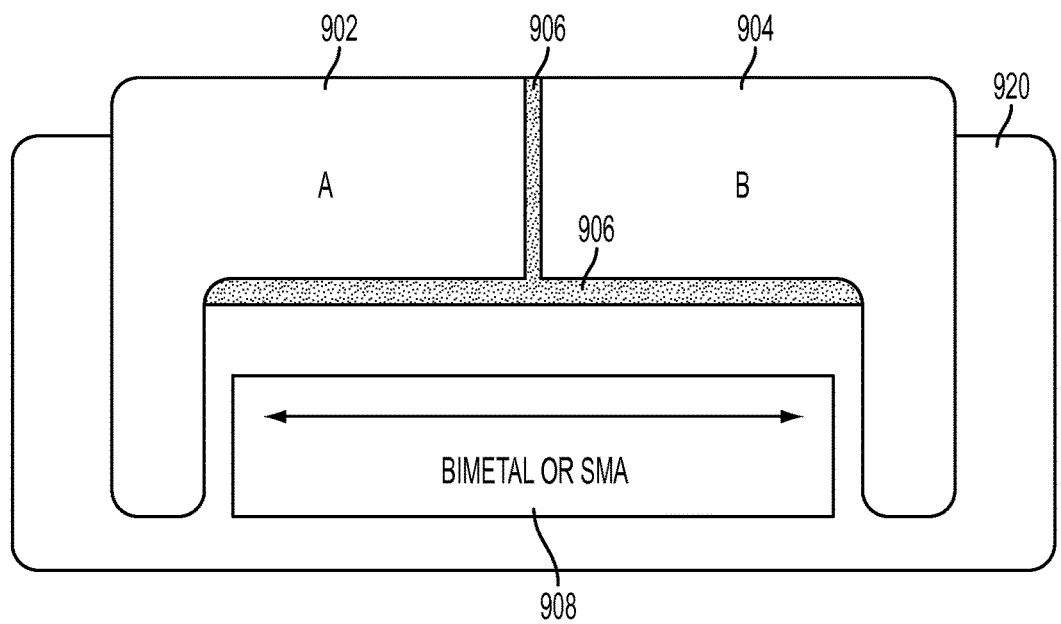
FIG. 9 is a front cross-sectional view of one embodiment of an end effector electrode that includes a temperature dependent conducting switch.

FIG. 9 illustrates another alternative embodiment of a temperature dependent switch that utilizes properties of bimetals or shape memory alloys to selectively couple electrodes or portions of an electrode having a single continuous conductive surface based on temperature. In particular, FIG. 9 illustrates a first electrode portion 902 and a second electrode portion 904 that are separated from one another over at least a portion of the electrode by an electrical insulator 906. The first and second electrode portions 902, 904 can be coupled to, for example, a jaw member 920 of an end effector, and in some embodiments can include a mirrored configuration on an opposing jaw member (not shown). The first electrode portion 902 can be coupled to an electrical signal generator and can be in contact with a bimetal or shape memory alloy switch 908. The switch 908 can be separated from the second electrode portion 904 by, for example, an air gap. As the first electrode portion 902 is heated by the electrical signal generator via ohmic heating (and via conduction from the tissue it contacts), thermal energy can be transferred to the bimetal or shape memory alloy switch 908. The switch 908 can expand as its temperature increases until it is in contact with both the first electrode portion 902 and the second electrode portion 904. At such a time, the switch 908 can conduct electricity between the first and second electrode portions 902, 904. Such a configuration can be advantageous because less power is required to heat the solely the first electrode portion upon initiation of a sealing operation, thereby effectively treating a small portion of the tissue before treating the entire targeted area.

Methods for controlling temperature in an electrosurgical instrument are also provided herein. In an exemplary embodiment, such a method can include positioning an end effector as described above such that tissue is disposed between first and second jaw members of the end effector. The method can further include applying electrical energy to an electrode disposed between the tissue and one of the first or second jaw members to create a plurality of thermal zones having varying temperatures. As described above, the electrode can have a single continuous conductive surface, but can include any number of openings formed therein and/or electrical insulators coupled thereto that have varying thermal conductivities such that applying energy to the electrode creates the varying thermal zones. Further, the thermal zones can be arranged in any of a variety of patterns or orientations. For example, in some embodiments a first thermal zone and a second thermal zone can extend along a longitudinal axis of the end effector, and the second thermal zone can be positioned laterally of the first thermal zone and have a lower temperature than the first thermal zone. In other embodiments, a first thermal zone and a second thermal zone can be created and the second thermal zone can be positioned at a distal end of the end effector such that a lower temperature is present at the distal end of the end effector. In other embodiments, however, the orientation of the first thermal zone and the second thermal zone can be reversed to create a high temperature thermal zone at the distal end of the end effector.

The various devices described herein can be formed from a number of materials and can have a variety of shapes, sizes, and configurations. For example, the various electrical insulators described herein can be formed from any of a variety of polymers (e.g., grivory) or ceramics, and can be selected such that desired coefficients of thermal conductivity are achieved. For example, electrical insulators having relatively higher thermal conductivity can include aluminum with an oxide layer formed thereon that provides electrical insulation via the oxide layer while the aluminum conducts heat. Exemplary electrical insulators having relatively lower thermal conductivity can include most plastics (which are often both electrical and thermal insulators), such as Vectra® and other liquid crystal polymers (LCP), polyether ether ketone (PEEK), and polyimide, among others. Electrical and thermal conductors described herein can also be formed from a variety of other materials known in the art, including, for example, stainless steel, aluminum, copper, tungsten, silver, and titanium.

The temperature dependent selectively conductive materials described herein can be, for example, materials having a conductive-resistive matrix that dynamically varies electrical conductivity based on temperature. The conductive-resistive matrix of a PTC or NTC material can include, for example, a polypropylene or a medical grade silicone polymer that is doped with conductive particles (e.g., carbon). Polymer PTC or NTC materials are known in the field of over current protection devices that will "trip" and become resistant when a selected trip current is exceeded. Further information on temperature dependent selectively conductive materials (e.g., PTC and NTC materials) can be found in U.S. Pat. Nos. 7,083,619 and 7,112,201, which are incorporated by reference in their entirety above.

The devices described herein can have a number of advantages over alternative approaches that utilize multiple electrodes (often having multiple polarities). For example, device and manufacturing complexity can be minimized by utilizing an electrode with a single continuous conductive surface. By way of further example, electrical insulators can be formed from a molded polymer or coating, or can be plasma-sprayed as a thin ceramic coating, etc. In some embodiments, an electrode and plastic electrical insulator can be over-molded to form a single part for assembly. Still further, openings can be formed in an electrode using any of a number of processes, including laser cutting, Electrical Discharge Machining (EDM), etc.

The devices described herein can be designed for multiple uses and can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the instruments described herein will be processed before surgery. First, a new or used instrument can be obtained and, if necessary, cleaned. The instrument can then be sterilized. In one sterilization technique, the device can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. In other embodiments, sterilization can be performed using any number of ways known to those skilled in the art including beta radiation, ethylene oxide, steam, or a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical end effector, comprising:
first and second jaw members movable relative to one another between an open position and a closed position to clamp tissue therebetween;
an electrode having a single continuous conductive surface coupled to the first jaw member such that the electrode contacts tissue clamped between the first and second jaw members when in the closed position; and
a plurality of electrical insulators disposed between the electrode and the first jaw member coupled thereto, the plurality of electrical insulators including a first electrical insulator having a first thermal conductivity and a second electrical insulator having a second thermal conductivity that is higher than the first thermal conductivity, wherein at least one of the first thermal conductivity and the second thermal conductivity is constant, and
wherein the electrode is divided into a plurality of thermal zones by at least one opening formed therein, the plurality of thermal zones including a first thermal zone and a second thermal zone, and the plurality of electrical insulators are arranged such that the first thermal zone contacts the first electrical insulator and the second thermal zone contacts the second electrical insulator.

2. The surgical end effector of claim 1, wherein the first thermal zone and the second thermal zone extend along a longitudinal axis of the end effector, and wherein the second thermal zone is positioned laterally outward of the first thermal zone.

3. The surgical end effector of claim 1, wherein the first thermal zone and the second thermal zone extend along a longitudinal axis of the end effector, and wherein the first thermal zone is positioned laterally outward of the second thermal zone.

4. The surgical end effector of claim 1, wherein the first thermal zone and the second thermal zone are positioned alternately along a longitudinal axis of the end effector.

5. The surgical end effector of claim 1, wherein the first thermal zone is positioned at a distal end of the end effector.

6. The surgical end effector of claim 1, wherein the at least one opening formed in the electrode includes a slit extending along a longitudinal axis of the end effector.

7. The surgical end effector of claim 1, wherein the at least one opening formed in the electrode includes a slit that is transverse to a longitudinal axis of the end effector.

8. The surgical end effector of claim 1, wherein at least one of the plurality of electrical insulators is disposed within the at least one opening formed in the electrode to separate the plurality of thermal zones of the electrode from one another.

9. The surgical end effector of claim 1, further comprising a temperature dependent selectively conductive material disposed within the at least one opening formed in the electrode.

10. The surgical end effector of claim 9, wherein the temperature dependent selectively conductive material is a Positive Temperature Coefficient (PTC) material.

11. The surgical end effector of claim 9, wherein the temperature dependent selectively conductive material is a Negative Temperature Coefficient (NTC) material.

\* \* \* \* \*